United States Patent [19]

Larimer

[11] Patent Number: 4,565,396
[45] Date of Patent: Jan. 21, 1986

[54] PNEUMATIC CONTACT LENS INSERTION DEVICE

[76] Inventor: John M. Larimer, 311 Lindsey La., Pittsburgh, Pa. 15239

[21] Appl. No.: 710,707

[22] Filed: Mar. 11, 1985

[51] Int. Cl.⁴ .............................................. A61F 9/00
[52] U.S. Cl. ................................................... 294/1.2
[58] Field of Search .................. 294/1.2, 1.1, 20, 64.1; 128/300, 303; 206/5.1; 248/362, 363; 351/160

[56] References Cited

U.S. PATENT DOCUMENTS 4,026,591 5/1977 Cleaveland ........................... 294/1.2
4,093,291 6/1978 Schurgin ............................... 294/1.2

Primary Examiner—James B. Marbert

[57] ABSTRACT

An opthalmic insertion device for quick and accurate insertion of contact lenses with minimum handling. A pneumatic insertion device comprises a main cylindrical body having a coil spring driven piston for pumping air fitted into and substantially filling cross sectionally a forward area of the main body cylinder, a hollow shaft axially slidable communicating the area behind the piston to an area within a soft rubber cup on the forward end of the said shaft, a buffer spring to limit the retraction of the hollow shaft into the cylinder, a cocking plunger fitted into and substantially filling cross sectionally a rear portion of the cylinder provides a means to compress the piston drive spring and is provided with a rearward biasing spring to automatically return the said cocking plunger to a rear position of the main body cylinder, a trigger device to hold said piston in the cocked position until a contact lens is ready to be inserted.

8 Claims, 8 Drawing Figures

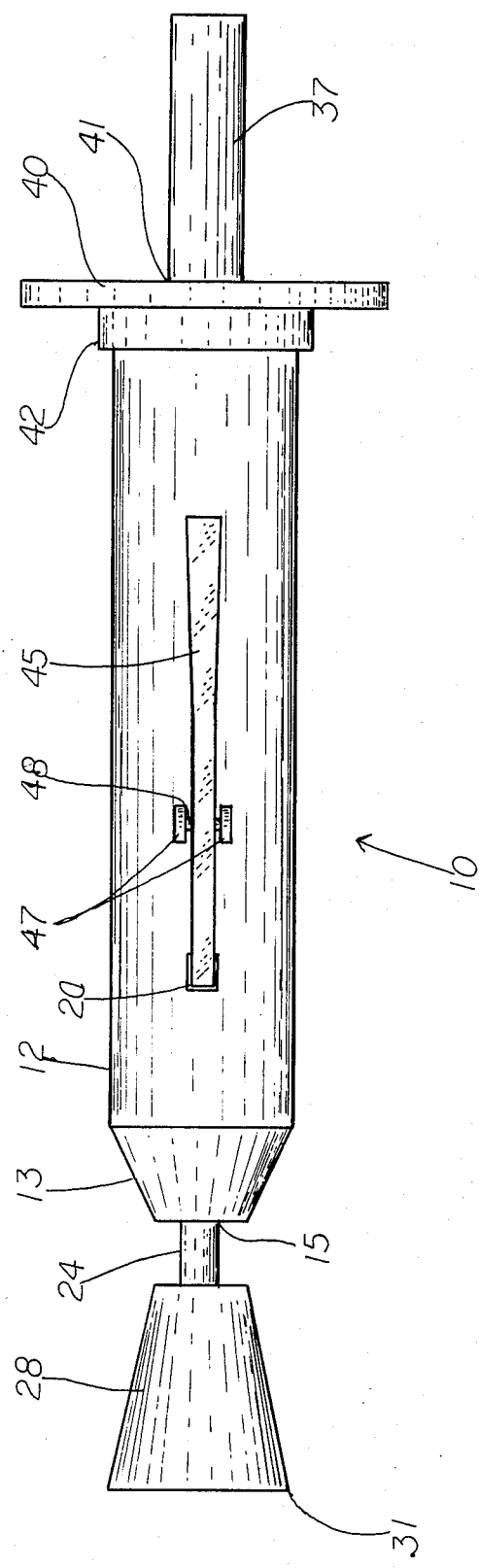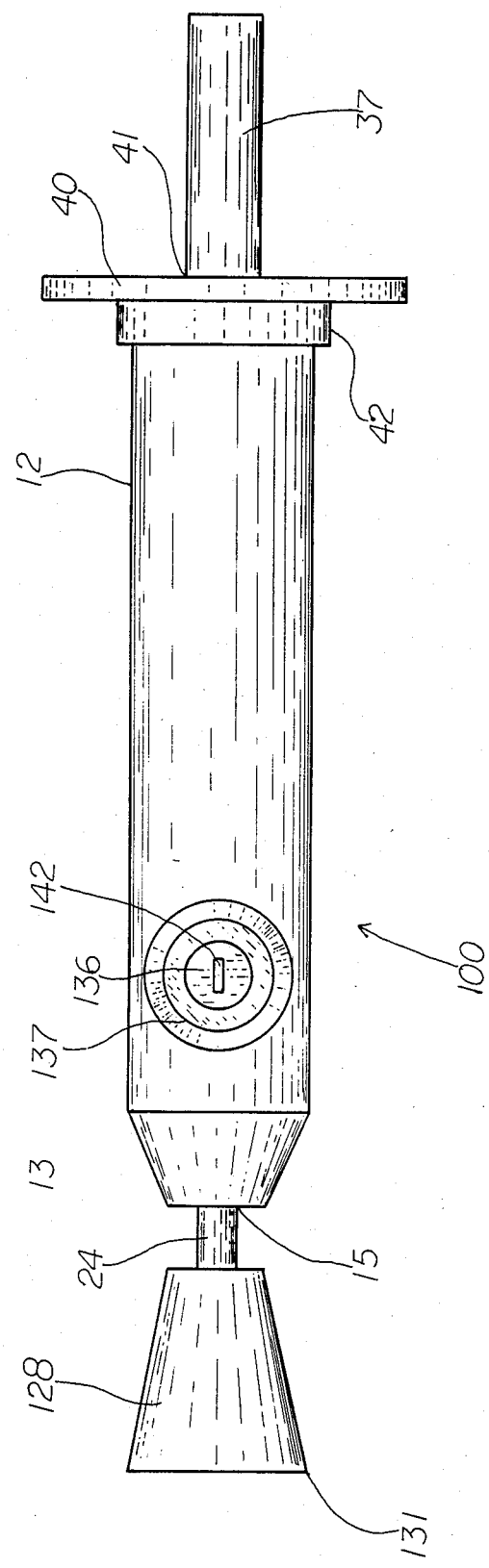

PNEUMATIC CONTACT LENS INSERTION DEVICE

BACKGROUND OF THE INVENTION

The present inventon relates to an opthalmic insertion device, and particularly to an insertion device which can insert a contact lens onto the surface of the eye, and more particularly to a contact lens insertion device which can insert a soft and flexible contact lens quickly, accurately, and with a minimum of handling.

The present customary method of inserting a contact lens requires that the previously cleaned and sterilized lens be removed from it's sterilization case by the hand and manually placed upon the tip of one finger and then with the eye lids held open the lens is touched to the eye whereupon if the surface contact between the lens and the eye is greater than that between the finger and the lens, the contact lens will remain smoothly fixed to the surface of the eye. However, it often occures that the lens becomes mispositioned on the finger tip due to various reasons such as premature contact with the eye lid or eye lash, or slippage from the finger tip. When mispositioning occures, an imperfect placement of the lens occures, or the lens is placed in the eye in a folded state, or the lens falls from the finger. Such unsuccessful insertions are not only troublesome and untimely, but sometimes result in the lose of the lens. Furthermore, modern soft contact lenses are plyable enough to become distorted when placed upon the convex surface of the finger. It is important that this distortion does not occure because it interferes with the contact between the lens and the eye. On the tip of the properly wetted finger the lens assumes a slight convex curvature in the center of the lens where a smooth concave curve is most desirable, and sometimes this distortion is so severe that the lens will actually turn inside out and fold over the finger tip making it impossible to apply to the eye. Thus it can be seen that unsanitary and mechanically difficult problems arrise when applying contact lenses by the customary method.

Furthermore, with the present mode of insertion it is difficult or impossible for people with certain debilitating phyical conditions to insert a contact lens themselves, and also difficult and unsanitary for another to perform for them.

Furthermore, much valuable time is lost by doctors, technicians, and patients while trying to insert a contact lens for the first time in the doctor's office in order that an initial examination can be made. Many patients become frustrated after several unsuccessful attempts making the initial insertion even more difficult.

Furthermore, the extended wear type lenses require a greater degree of cleanliness in order to extend their wearing time to that which the lens is designed for. Difficulty in handling and inserting these lenses subjects them to contamination and abrasion shortening the wearing time and the life of the lens.

According to the present invention, there is provided an insertion device which solves these problems in a manner yet unknown. The present invention inserts the contact lens mechanically with a greater degree of accuracy than the insertion done by the finger tip. The present invention has at it's tip a soft rubber cup providing a narrow circular area of contact with the lens, allowing the contact lens to assume it's natural shape while it is being inserted. With the present invention the soft rubber cup and a buffer spring provide a gentle cushioning effect minimizing eye irritation and the possibility of eye injury. With the present invention an accurate placement of the contact lens on the eye surface is accomplished quickly and before eye reflexes can interfere.

Another object of the invention is to provide an insertion device by which a person can easily insert a contact lens onto the eye of another person quickly accurately, and sanitarily. This would be of importance to people desiring to have the advantages of wearing contact lenses, but unable to install the lens themselves.

Another object of the invention is to provide a means of conveying the contact lens from it's sterilization case to the eye without handling by the fingers. With the present invention a plunger is provided which creates a vacuum within the rubber insertion cup which can be used to withdraw a lens from a properly designed sterilization case.

Still other objects, features, and attendant advantages of the present invention will become apparent from a reading of the present specifications, or from the practice of the invention herein disclosed.

SUMMARY OF THE INVENTION

Briefly, the above advantages are obtained in accordance with the present invention by providing a device for the insertion of contact lenses. The present invention comprises a main cylindrical body having within it a coil spring driven piston, an air compression area, a buffer spring located within the compression area, a cocking plunger extending rearward from the compression area out of the main body cylinder a sufficient distance, a third coil spring biasing rearward the cocking plunger, a retractable hollow sliding shaft entering the front portion of the main body cylinder and sliding axially through the center of the piston into the compression area, communicating the compression area with the area within a soft rubber cup located on the forward end of the sliding shaft, a triggering device to catch and hold the piston in the cocked position and mechanically able to release the piston on demand.

The present invention permits the withdrawal of a contact lens from a suitably designed sterilization case by depressing the cocking plunger until the piston becomes locked with the trigger and then releasing the cocking plunger to return rearward, whereby creating a vacuum within the rubber cup which can be applied to sucking a contact lens from it's case onto the lip of the rubber cup.

The contact lens is then brought to the eye while adhering to the lip of the rubber cup. When contact is made between the eye and the contact lens, the trigger is activated allowing the piston to be driven rearward causing a positive pressure to be forced from the compression chamber through the hollow shaft to behind the contact lens. The lens is then propelled pneumatically onto the surface of the eye as the rubber cup and hollow shaft are driven rearward by the force of the piston coil spring.

BRIEF DESCRIPTION OF THE DRAWINGS

FIG. 3 showing the cocking plunger returned to it's rearward position and a contact lens drawn onto the rubber cup and the sliding shaft partially retracted;

FIG. 7. is a planar view of the preferred embodiment as view from the top;

FIG. 8. is a top planar view of the alternate embodiment of FIG. 6.

DESCRIPTION OF THE PREFERRED EMBODIMENT

Figure 1:
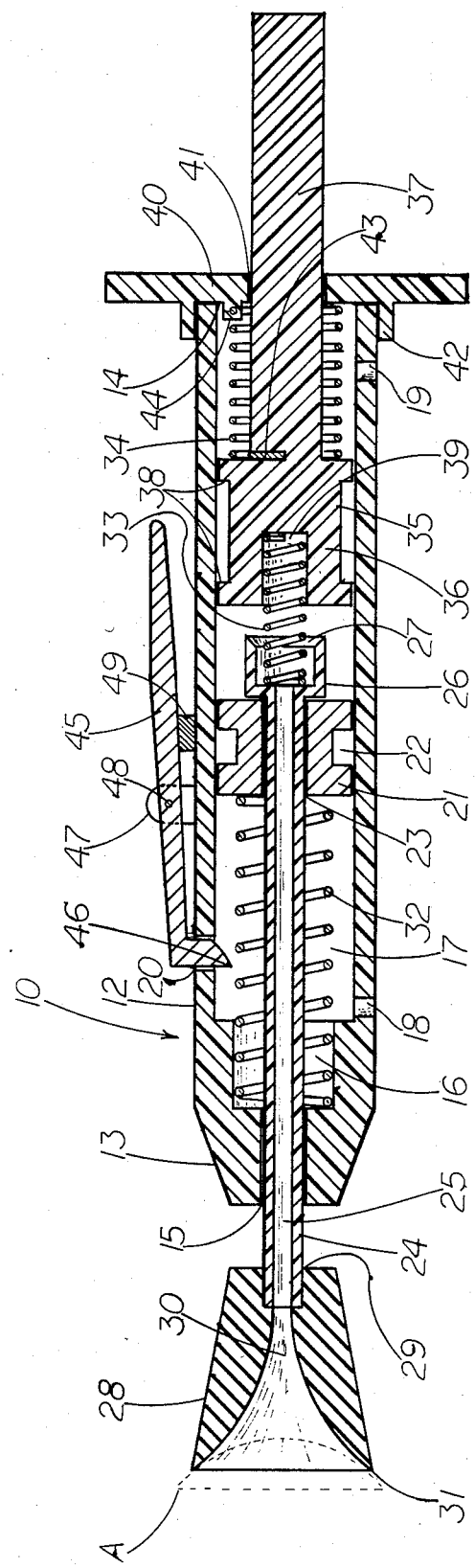
FIG. 1. is a longitudinal sectional view of the preferred embodiment of the present disclosed invention.
Figure 2:
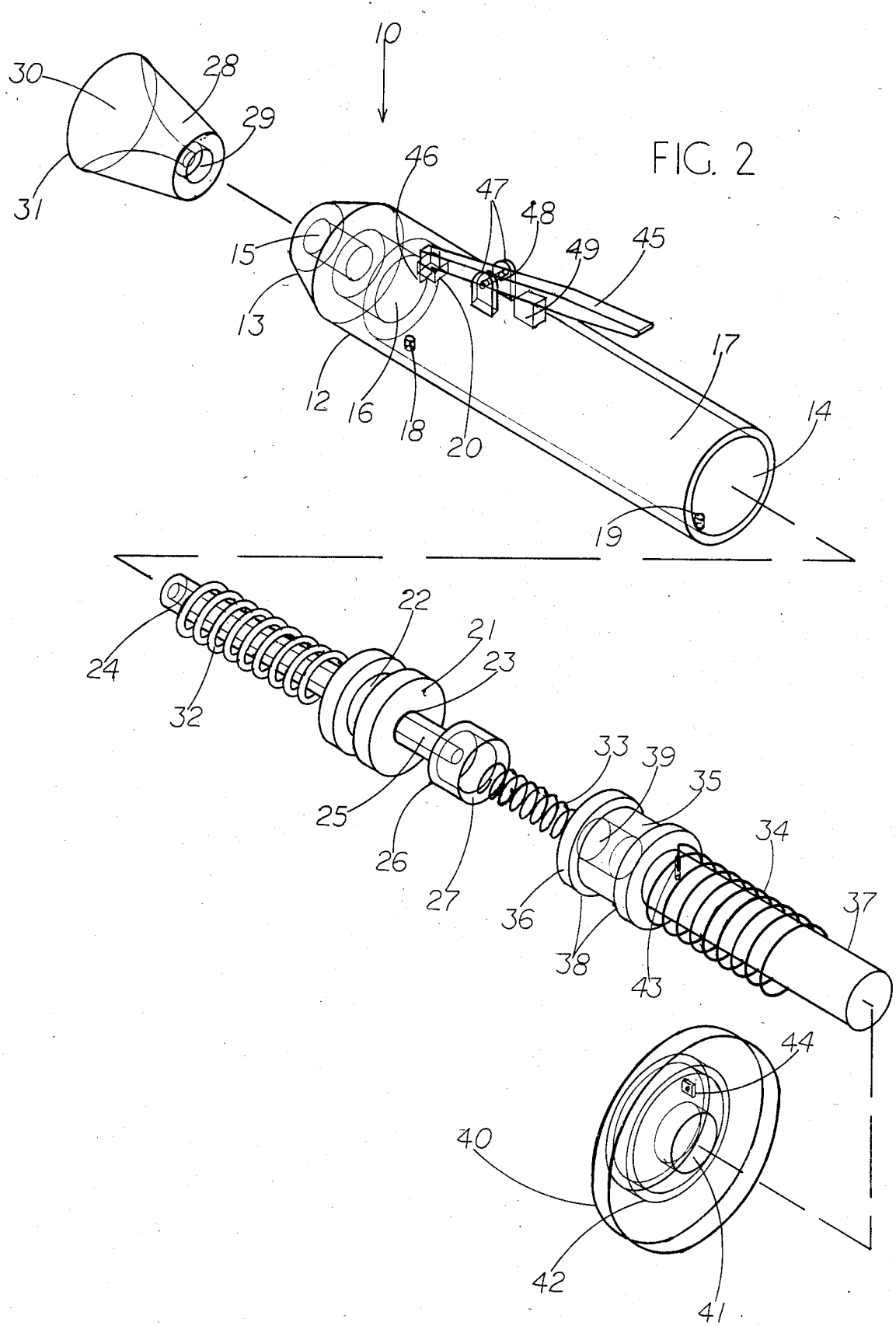
FIG. 2. is an exploded perspective view of the preferred embodiment shown in transparent form.

Referring to FIGS. 1, 2, and 7. of the drawings, a preferred embodiment of the present invention is shown which is a pneumatic contact lens insertion device for the insertion of contact lenses, and particularly the insertion of soft type contact lenses. The preferred insertion device, generally designated 10, includes a main body 12, which is generally cylindrical in form and being conically tapered in the front 13, and open at the rear 14. The main body 12 is preferably made of an inexpensive, easily molded plastic such as polypropylene. The main body 12 has at it's tapered end 13 a smooth bore passage 15, cylindrical in form and extending axially and longitudinally rearward and terminating at the forward end of a second and greater diameter bore 16. Bore 16 is also cylindrical and extends axially and longitudinally rearward and terminates at the forward end of the main bore 17. Main bore 17 extends rearward axially and longitudinally and ends at the open rear end of the main body 12. There is provided a vent hole 18, which is cylindrical in form and communicates the area within the main bore 17 with the outside of the main body 12. Hole 18 passes radially through the wall of the main body 12 at the forward most end of the main bore 17. A second vent hole 19, having the same description as hole 18 is located near the rear of the main body 12, but forward of the end cap 40 which will be described later. There is also provided a third hole 20, which is substantially square in form and communicates throught the wall of the main body 12 into the main bore 17. Hole 20 is diametrically opposite hole 18, and located sufficiently rearward of the rear end of bore 16 a distance to be later specified.

Provided within the main bore 17 is piston 21, which is cross-sectionally circular and generally cylindrical in form. Piston 21 is preferably made of a low friction, easily molded plastic such as tetrafluoroethylene fluorocarbon polymer. Piston 21 substantially fills cross-sectionally the main bore 17, creating a partial gas seal therein while remaining free to easily slid within main bore 17. Piston 21 has a groove 22 molded or machined radially arround it's girth and longitudinally centered thereon. Groove 22 has a longitudinal width approximately equal to the difference of the radii of bore 16 and bore 17. A cylindrical bore 23 passes axially and longitudinally through piston 21 and is equal in diameter to bore 15.

A tubular shaft 24 passes through bore 23 and forward through bore 16 and out of the tapered front portion of the main body 13 through bore 15. Shaft 24 is open at both ends and communicates an area of the main bore 17 behind piston 21 with the inner area 30 of rubber cup 28. Shaft 24 is generally tubular over the majority of it's length, having an outside cross-sectional diameter slightly less than the diameter of bore 15 and bore 23 so that the forward end of shaft 24 can slide freely through bore 15 and bore 23. Shadft 24 is preferrably made of a rigid, easily molded plastic such as polypropylene. Shaft 24 has an inner passage 25 of sufficient bore to communicate a charge of air and small enough to leave the wall of shaft 24 of a sufficient thickness to maintain it's rigid integrity. Shaft 24 terminates at the rear end with a cylindrical flange 26. Flange 26 is to be an integrally molded part of shaft 24, and is to function as a stop for piston 21, limiting the distance piston 21 can slid rearward. Flange 26 has an outside diameter greater than bore 23 but less than bore 17, and an inside diameter greater than the width of buffer spring 33. Flange 26 is open at the rear and terminates with a tapered lip 27, which slopes inward and forward into the hollow inside surface of flange 26. The forward end of shaft 24 terminates within a molded hollow 29 of the rubber cup 28.

Rubber cup 28 is the portion of the present invention 10 which mounts and holds a contact lens A. Rubber cup 28 is preferrably made moldable soft rubber such as a silicone type rubber. Rubber cup 28 is bonded to shaft 24 within hole 29 by a suitable adhesive. Rubber cup 28 is cross-sectionally circular and longitudinally conical on it's outer surface, and tapers rearward to a flattened end of a diameter approximately equal to the forward end of the main body 13. Rubber cup 28 has a hollow interior 30 defined in the forward end by lip 31 and in the rear by bore 25 in shaft 24. The surface of interior 30 of rubber cup 28 has an inward curving funnel shape, broadest at lip 31 and narrowest at the point which communicates with the hollow passage 25 Of shaft 24. The outer surface of cup 28 meets the inner surface to form the cup's lip 31. It is upon lip 31 that a contact lens A is mounted in preparation for insertion. Lip 31 provides a non-abrasive, form fitting area of minimum contact between invention 10 and a contact lens A. The funnel shaped interior 30 of rubber cup 28 is intended to evenly disperse a charge of air coming from behind piston 21 through shaft 24 evenly over the rear surface of contact lens A, thereby propelling contact lens A smoothly onto the eye.

There is provided within the main body bore 16 and into bore 17 a piston drive spring 32, which is a coil spring having an outside diameter equal to bore 16 and providing a rearward biasing force upon piston 21. Spring 32 is housed within bore 16 when the spring 32 is fully compressed, but extends out of bore 16 into bore 17 against the forward end of piston 21 when spring 32 is in it's extended position. Spring 32 is axially positioned within the main body 12 and coils loosely around shaft 24 without contact so as not to impede the free movement of either shaft 24 or piston 21 therein.

There is provided a cocking plunger 35, which extends into the rear open end 14 of the main body 12, substantially filling cross-sectionally bore 17 so as to form a reasonable gas seal and yet fit loosely enough to slide freely therein. Plunger 35 is cross-sectionally circular and generally cylindrical in form, having a head 36 housed within bore 17, and a narrower stem 37 extending out of the main body 12 rearward. Plunger 35 is preferrably made of an inexpensive, easily molded plastic such as polypropylene. Plunger 35 has two radial belts or raises rings 38, 38, positioned one forward and one rearward on head 36, and function to provide a reasonable gas seal while limiting the frictional contact between plunger head 36 and the inner wall of the main body 12. Rings 38, 38 could be integrally molded with plunger 35 or be made of a soft rubber such as butyl rubber and be bonded thereon. Axially centered within the forward end of head 36 is provided a cylindrical cavity 39, open in the front end and closed at the rear end, having a bore diameter equal to the outside diameter of the buffer spring 33. Bore 39 is provided to secure and guide spring 33. Buffer spring 33 is a coil spring provided to limit the rearward travel of shaft 24, and has an outside diameter small enough to be freely received into flange 26. Spring 33 provides a forward biasing force less than the rearward biasing force of spring 32 so that spring 32 is able to partially compress spring 33 when spring 32 is substantially extended rearward.

Stem 37 of plunger 35 extends out the rear of the main body through hole 41, hole 41 being axially centered in the main body end cap 40. End cap 40 is cross-sectionally circular and has a diameter greater than the outside diameter of the main body 12, and is provided to function as a guide for the plunger stem 37 and an anchoring base for the coil spring 34, coil spring 34 providing a rearward biasing force to plunger 35. End cap 40 has on it's forward face an integrally molded cylindrical flange 42 which tightly fits radially around the girth of the main body 12. Rearward biasing coil spring 34 is provided with an outside diameter less than that of bore 17 and an inside diameter greater than that of plunger stem 37. When extended, spring 34 has sufficient strength to overcome the contact friction of plunger 35 and the main bore 17 wall, and return plunger 35 to it's rearmost position. Spring 34 is anchored at it's forward most end into a small bore 43, which extends radially into stem 37 just rearward of head 36. Spring 34 is anchored at it's rearward end through a small tab protrusion 44, which is integrally molded with cap 40 and located inboard of flange 42 so as to fit inside bore 17 at the end of main body 12.

Vent hole 19 is located just forward of the forward end of flange 42 and is provided to equalize pressure within bore 17 behind plunger head 36.

There is provided in the preferred embodiment of the present invention a trigger 45 to catch and hold piston 21 when it is in the cocked position. Trigger 45 comprises a lever which is substantially square cross-sectionally, and is preferably made of a hard, easily molded plastic or a light weight metal of a noncorrosive type. The tip 46, of trigger 45, extends through the main body 12 and into bore 17 through square hole 20, which is located rearward of the rear end of bore 16 a distance approximately equal to half the longitudinal length of piston 21. Trigger tip 46 is pointed on it's forward edge and rounded on it's rear edge so as to be able to ride up over the forward edge of piston 21, and drop into groove 22, locking piston 21 in the cocked position. Trigger 45 when viewed longitudinally passes out of the main body 12 through hole 20 upward a short distance and forms a ninty degree angle and then extends rearward a distance approximately equal to half the overall length of the main body 12. Approximately one third rearward along the length of the trigger 45 from the hole 20, are located two tabs 47, 47. Tabs 47, 47, are integrally molded with the main body 12, and run longitudinally parallel and upward from the main body 12 outer surface a distance sufficient to provide an upward sloping posture to trigger 43 with respect to the outer surface of the main body 12 when fixed thereon. Tabs 47, 47 are spaced apart a distance slightly greater than the width of trigger 45. Trigger 45 and tabs 47, 47 are bored axially through so that a small metal shaft 48 can be inserted through tab 47, trigger 45, tab 47, Shaft 48 provides a pivot point for trigger 45 so that the trigger 45 can be longitudinally rocked upon the main body 12. The rear portion of trigger 45 behind pivot shaft 48 is biased upward and the trigger tip 46 is biased downward into hole 20 by a soft rubber pad 49, which is located just behind the tabs 47, 47.

Figure 3:
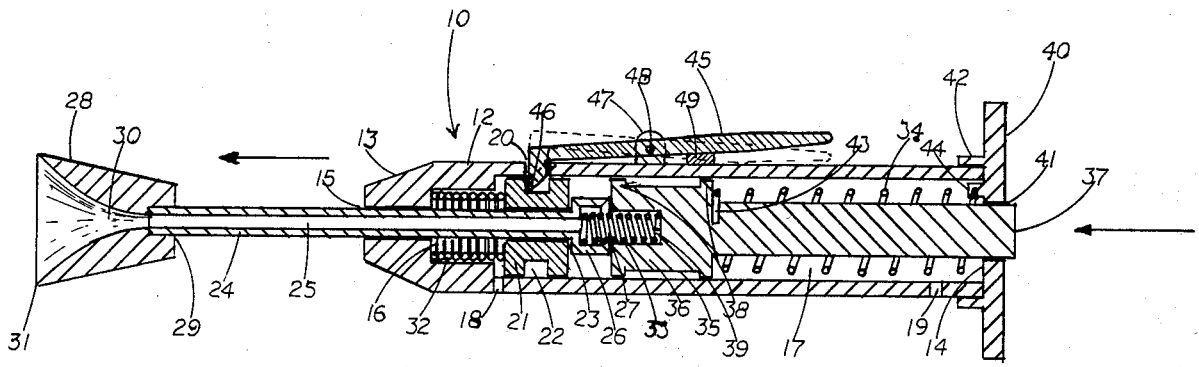
FIG. 3. is a longitudinal section view as in FIG. 1. showing the preferred invention with the cocking plunger depressed and the piston locked with the trigger.
Figure 4:
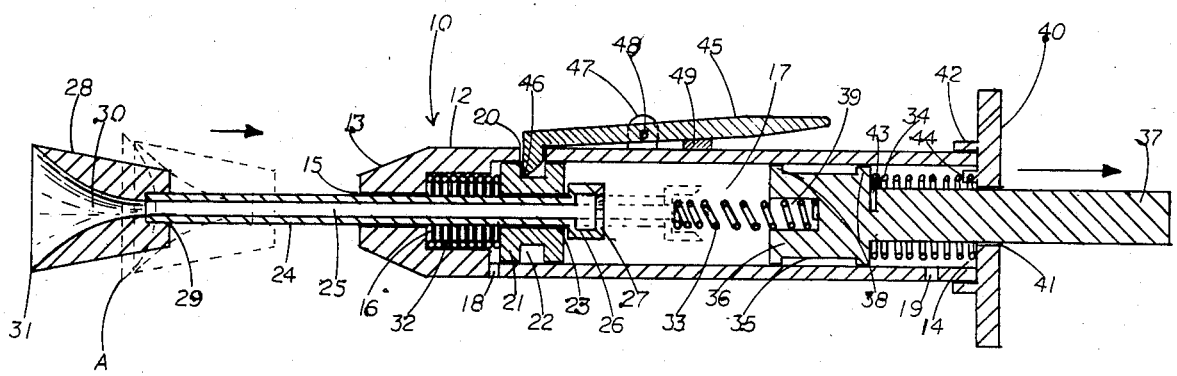
FIG. 4. is a longitudinal sectional view as in FIG. 1.
Figure 5:
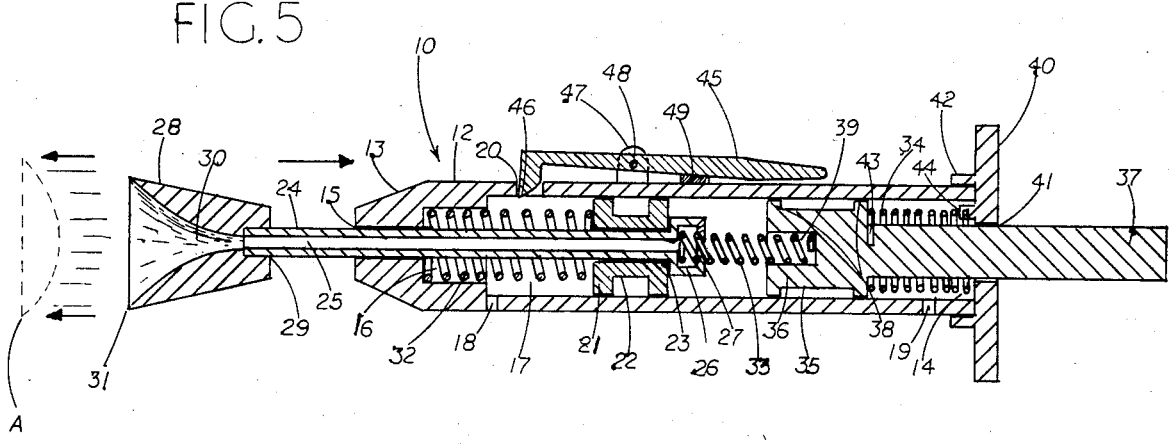
FIG. 5. is a longitudinal sectional view as in FIGS. 1, 3, and 4. showing the trigger depressed and the piston propelled rearward and the contact lens being ejected.

Referring now to FIGS. 3, 4, and 5, a series of drawings of the preferred form of the present invention demonstrates the opperation of the invention. The embodiment of the present invention is taken into hand and plunger 35 is depressed into the main body 12 by the index finger while the main body 12 is supported by the thumb and seconde finger.

Referring in particular to FIG. 3, plunger 35 has been depressed to it's fullest extent and can not be pushed into the main body 12 any further. At this point, spring 34 is fully extended, spring 33 is fully compressed, flange 26 and the plunger head 36 are touching, piston 21 is fully forward and spring 32 is fully compressed into bore 16, shaft 24 and rubber cup 28 are extended fully forward, and trigger tip 46 has rode up over the edge of piston 21 and has dropped into place in groove 22.

Referring now to FIG. 4. While the cocking plunger 35 is still depressed, rubber cup 28 is touched to the outside surface of contact lens A while in it's sterilization container. A slight pressure is maintained on the surface of contact lens A by the rubber cup 28 as the cocking plunger 35 is released to be pulled rearward by the cocking plunger spring 24. With piston 21 locked forward and the cocking plunger 35 being drawn rearward, a slight vacuum is created within bore 17 between the cocking plunger 35 and the piston 21 which is communicated to the area 30 within rubber cup 28 through passage 25 of shaft 24. The vacuum created is sufficient therein to draw the contact lens A onto the lip 31 of the rubber cup 28. During the retraction of plunger 35, shaft 24 is pushed into contact with the forward end of buffer spring 33. At this point it is assumed that the contact lens A has been successfully drawn onto lip 31 of the insertion device 10, and the shaft 24 is retracted and making contact with spring 33 within flange 26. The tapered lip 27 of flange 26 aids in guiding the buffer spring 33 into the hollow of flange 26.

Referring now to FIG. 5. it can be seen that the preferred invention 10 is ready for the insertion. While holding 10 between the thumb and index finger with the index finger on the rear end of trigger 45, the contact lens A is touched or at least brought very close to the open eye's surface while still upon the lip 31 of the rubber cup 28. If contact is made with the eye and the len A, shaft 24 and rubber cup 28 can further retract as buffer spring 33 further compresses. It is not necessary that contact lens A be actually touched to the eye for the preferred invention 10 is capable of projecting a lens onto the eye from a short distance away. With or without making eye contact, trigger 45 is depressed in the rear releasing pisto 21. As piston 21 is driven rearward by spring 32, a positive pressure is created within bore 17 between piston 21 and cocking plunger head 36. The resulting gush of air is forced out forward through passage 25 into the inner area 30 of the rubber cup 28. As the air is forced out through the funneled surface of 30, it must expand evenly over the back surface of the contact lens A, propelling lens A from the lip 31 evenly onto the surface of the eye. Simultaneously, the force of the drive spring 32 on piston 21 further drives shaft 24 and rubber cup 28 rearward away from the eye as buffer spring 33 is further compressed.

Figure 6:
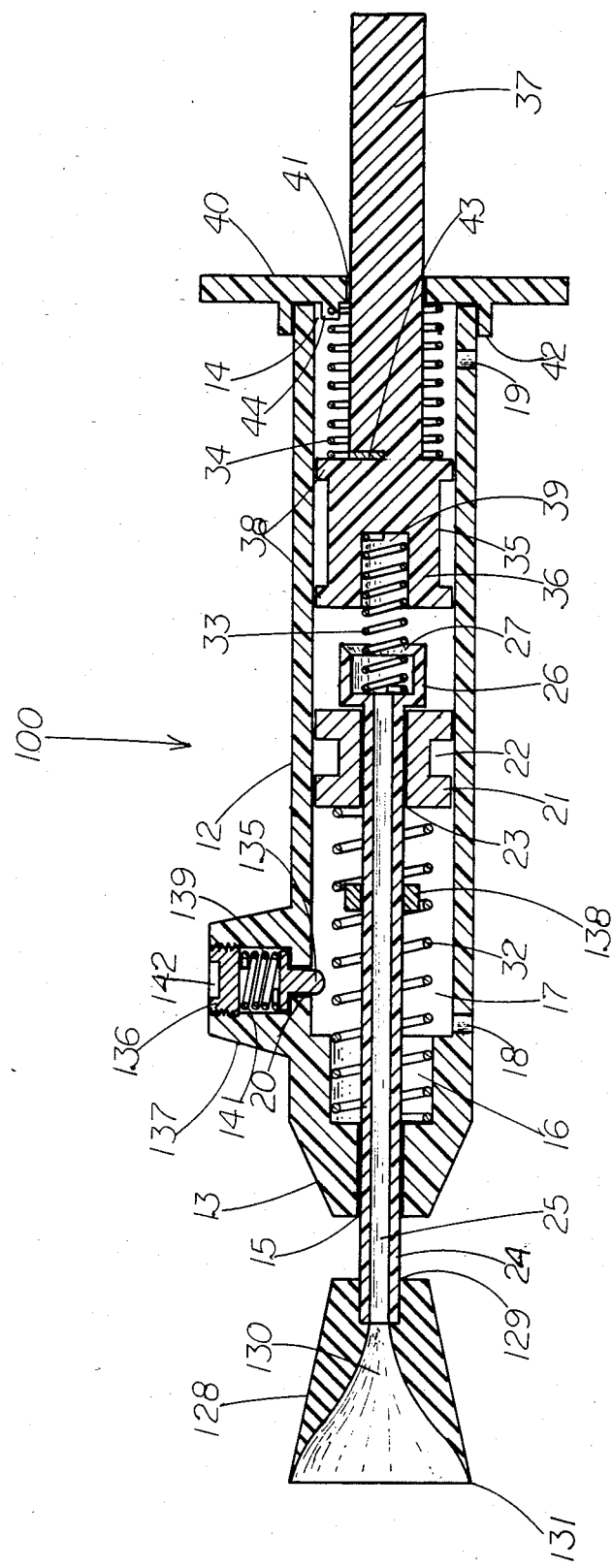
FIG. 6. is a longitudinal sectional view of an alternate embodiment showing an alternate trigger mechanism and an alternate rubber cup design.

Referring now to FIG. 6 and FIG. 8. An alternate embodiment of the invention is shown in which elements corresponding to those of the embodiment shown in earlier figures are correspondingly numbered. This alternate embodiment referred to as 100, provides an alternate triggering mechanism which can release piston 21 automatically by a pressure sensitive release. Alternate embodiment 100 also comprises a slightly different rubber cup 128 with an interior design made different to illustrate that the shape or design of the rubber cup 128 can be varied.

In the alternate embodiment 100, there is provided a conical protrusion 137 to house the alternate trigger assembly. Protrusion 137 extends outward away from the main body 12 radially. Protrusion 137 is intregrally molded with the main body 12, and is positioned thereon like a saddle, conical in form, and tapering outward away from the main body 12. Protrusion 137 is hollow having a cylindrical bore 141 axially centered in protrusion 137 and extending into bore 17. The upper and outermost end of bore 141 is threaded so that a threaded cap 136 can be screwed therein. Cap 136 is provided with a slot 142 in it's top surface to facilitate adjustment by a small screwdriver. Inward of cap 136, bore 141 is smooth and has within it a coil spring 139. Spring 139 provides a downward biasing force on the trigger stud 135. Stud 135 is circular and has a flattened top which substantially fills bore 141 cross-sectionally, and a narrow stem which protrudes into the main bore 17 with a rounded tip which is hemispherical in form with a diameter equal to the diameter of the stem of stud 135. The rounded bottom of stud 135 extends into the main bore 17 far enough to engage groove 22 and lock piston 21 in the cocked position. A sufficient pressure asserted on piston 21 causes stud 135 to be pushed upward, compressing coil spring 139 and allowing piston 21 to be released rearward. There is provided a ring 138, pressed or bonded onto shaft 24 in an appropriate position to assert the fore mentioned pressure on the forward end of piston 21 to activate the release thereof. The amount of pressure required to push stud 135 upward and therefore release piston 21, can be varied by screwing in or out the cap 136 therby varing the downward biasing tention of spring 139.

There is also provided in the alternate embodiment 100, an alternate rubber cup 128 with a slightly different interior design 130. Interior 130 is funnel shaped but provides an ultra thin lip 131.

In opperation of the alternate embodiment 100, the contact lens is touched to the eye upon lip 131 of rubber cup 128 and a slight pressure asserted brings ring 138 to press against piston 21 causing stud 135 to be lifted upward and releasing piston 21 to be driven rearward propelling pneumatically the contact lens onto the eye.

Thus, it can be seen that the invention provides a means of inserting a contact lens onto the eye pneumatically, quickly and accurately. There is also provided a means of inserting a contact lens without touching the lens prior to insertion, which makes for a more sanitary insertion.

It is not intended that the present invention described herein be limited to or by the aforsaid description and related drawings of the two embodiments thereof, but only to the subject matter claimed hereinafter and it's equivalents.

What is claimed is:

1. A hand held mechanical device for pneumatically inserting contact lenses onto the surface of the eye with little or no handling of the contact lenses by the fingers during the insertion, said device comprising;

a cylindrical main body being open in the rear and tapered at the front, with said tapered front having a hole adapted to receive freely therein a hollow sliding shaft, said hole extends axially into the inside chamber of the said main body, and said main body having an end cap adapted to fit thereon, with said end cap having an axially centered hole passsing therethrough, and said main body having provided on it's outer surface a means of securing thereto a trigger assembly, and said main body having two vent holes with one said vent hole disposed forward and passing radially through the wall of the said main body, and said second vent hole being disposed rearward and passing radially through the wall of the said main body, and said main body having a square hole passing radially through the wall of the said main body and being disposed to fit therethrough a trigger tip;

a piston adapted to slide freely within the said main body and having a means for forming a partial gas seal between the said piston and the inside wall of the said main body, and said piston having a radial groove around it's girth providing a means of locking the said piston in a specified position within the said main body, and said piston having an axially centered hole through it's center so that a tubular shaft can slide freely therethrough;

a first coil spring disposed within the said main body forward of the said piston and providing a rearward biasing force to the said piston, and said first spring having a means of being retained axially centered within the said main body;

a cocking plunger disposed within the rear area of the said main body and slideable therein, and said cocking plunger having a head with a means for forming a partial gas seal between the outside surface of the said cocking plunger head and the inside surface of the said main body, and said plunger having a stem extending outward and rearward through the said end cap hole;

a second coil spring disposed within the said main body forward of the said end cap and coiling around the said cocking plunger stem and ending rearward of the said cocking plunger head, and said second spring having a means of being anchored at both ends with the forward end anchored to the said cocking plunger and the rearward end anchored to the said end cap, said second coil spring providing a rearward biasing force to the said cocking plunger;

a hollow sliding shaft having a longitudinal passage for air flow therethrough, with said shaft disposed through the said hole in the front tapered end of the said main body, freely slideable therethrough and extending into the interior of the said main body through the said hole in the said piston into the area between the said piston and the said cocking plunger head, and said shaft is provided with a flange on the rearward end to limit the rearward travel of the said piston thereon, and with said flange having an inward and forward tapering lip to guide a buffer spring;

a third coil spring disposed within the said main body between the forward end of the said cocking plunger head and the rear flanged end of the said sliding shaft, providing a forward biasing force limiting the rearward travel of the said sliding shaft, and said third spring having a substantially weaker biasing force than the said first spring, and said third spring having a means of being anchored within and guided by a hole provided axially centered in the forward face of the said cocking plunger head;

a trigger mechanism externally mounted on the said main body disposed in such a position so as to be lockable internally with the said piston groove when the said piston is in it's forward most position and said first spring is fully compressed;

a soft rubber cup disposed at the forward end of the said sliding shaft providing a means of mounting and retaining thereon a contact lens, and said cup having an internal shape designed to disperse a charge of air flowing outward from the said passage of the said hollow sliding shaft;

2. An insertion device as recited in claim 1, wherein said trigger is a finger opperated lever having a pivot point disposed between the rear end of the said trigger and the locking tip of the said trigger, with the said trigger tip disposed through the said square hole in the wall of the main body and lockable with the said piston when the said piston is in it's forward most position, and said trigger having a biasing force provided behind the said pivot point biasing upward the rear end of the said trigger thereby forcing the said trigger locking tip downward into the said main body through the said square hole.

3. An insertion device as recited in claim 1, wherein said rubber cup is made of a soft silicone rubber, and is conical shaped outside and funnel shaped inside, and the outside surface and the inside surface of the said rubber cup meet to form a thin circular lip.

4. An insertion device as recited in claim 1, wherein said trigger mechanism is automatic releasing, said automatic trigger comprising a conical housing having disposed therein a fourth coil spring biasing downward into the inside of the said main body a trigger stud, said trigger stud being flattened on the top providing a broadened surface on which the said fourth coil spring to press, and the said stud narrowing on the bottom so as to be passable through the said square hole in the said main body, and said bottom of said stud being rounded and engageable with the said piston groove when the said piston is in it's forward most position, and said fourth spring having an adjustable tention upon the top of the said stud, with said tentioning adjustable by means of a screwable cap disposed within the top end of the said trigger housing.

5. An insertion device as recited in claim 4, wherein said rubber cup is made of a soft silicone rubber and is conically shaped on the outside and has a longitudinal cross-sectional compound curved funnel shape on the inside providing an ultra thin lip on the forward end of the said rubber cup.

6. An insertion devive as recited in claims 1 or 4, wherein said piston is made of a durable low friction plastic such as tetrafluoroethylene flourocarbon polymer.

7. A piston as recited in claim 6, wherein said piston is opperable rearward by a rearward biasing spring whereby said piston provides a means of forcing a charge of air forward through the said sliding shaft and into the interior of the said rubber cup.

8. An insertion device as recited in claims 1 or 4, wherein said cocking plunger is provided as a means of forcing the said piston into the forward locked position and engaged with the said trigger, and said cocking plunger providing a means of drawing a contact lens onto the said rubber cup by a vacuum created between the said piston and the said cocking plunger as the said second spring draws the said cocking plunger rearward after the said piston has been locked forward.

* * * * *